United States Patent
Hazama et al.

(10) Patent No.: US 10,939,919 B2
(45) Date of Patent: Mar. 9, 2021

(54) HEMOSTATIC DEVICE

(71) Applicant: TERUMO KABUSHIKI KAISHA, Tokyo (JP)

(72) Inventors: Kenichi Hazama, Bear, DE (US); Ryosuke Maeda, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 400 days.

(21) Appl. No.: 15/642,995

(22) Filed: Jul. 6, 2017

(65) Prior Publication Data
US 2018/0008282 A1    Jan. 11, 2018

(30) Foreign Application Priority Data

Jul. 6, 2016  (JP) .............................. JP2016-134605

(51) Int. Cl.
*A61B 17/135*  (2006.01)
*A61B 17/132*  (2006.01)
*A61M 39/22*  (2006.01)
*A61B 17/00*  (2006.01)

(52) U.S. Cl.
CPC ........ *A61B 17/135* (2013.01); *A61B 17/1325* (2013.01); *A61M 39/22* (2013.01); *A61B 2017/00907* (2013.01)

(58) Field of Classification Search
CPC .............................. A61M 38/22; A61B 17/135
See application file for complete search history.

(56) References Cited

U.S. PATENT DOCUMENTS

| 3,547,401 A * | 12/1970 | Ellmann ............... A61M 39/22 251/144 |
| 5,609,580 A | 3/1997 | Kwiatkowski et al. |
| 7,498,477 B2 | 3/2009 | Wada et al. |
| 7,886,782 B1 * | 2/2011 | Curtis .................. B65D 47/061 141/337 |
| 8,481,803 B2 | 7/2013 | Wada et al. |

(Continued)

FOREIGN PATENT DOCUMENTS

| JP | H08-299437 A | 11/1996 |
| JP | 2014-521368 A | 8/2014 |

(Continued)

OTHER PUBLICATIONS

Office Action (Notice of Reasons for Refusal) dated Feb. 4, 2020, by the Japanese Patent Office in corresponding Japanese Patent Application No. 2016-134605 and an English Translation of the Office Action. (8 pages).

*Primary Examiner* — Anh T Dang
(74) *Attorney, Agent, or Firm* — Buchanan Ingersoll & Rooney PC

(57) ABSTRACT

A hemostatic device has a band for being wrapped around a puncture site P of a wrist W, securing means for securing the band in a state where the band is wrapped around the wrist, an inflation portion that interlocks with the band, and that is inflated by injecting gas, and an injection portion that can inject gas into the inflation portion. The injection portion is disposed in the band, and is foldable so as to decrease a space formed inside the injection portion. The hemostatic device can thus inflate an inflation portion without using a separate dedicated instrument, which can prevent a hemostasis-requiring site from being unintentionally compressed more than necessary.

13 Claims, 15 Drawing Sheets

(56) References Cited

U.S. PATENT DOCUMENTS

| | | |
|---|---|---|
| 8,524,974 B2 | 9/2013 | Wada et al. |
| 8,759,603 B2 | 6/2014 | Wada et al. |
| 2013/0041303 A1 | 2/2013 | Hopman et al. |
| 2014/0012313 A1 | 1/2014 | Finkielsztein et al. |
| 2016/0338709 A1 | 11/2016 | Wada et al. |

FOREIGN PATENT DOCUMENTS

| | | |
|---|---|---|
| JP | 2014-200308 A | 10/2014 |
| WO | WO 2012/129146 A2 | 9/2012 |

\* cited by examiner

HEMOSTATIC DEVICE

CROSS-REFERENCE TO RELATED APPLICATION

This application claims priority to Japanese Application Number 2016-134605 filed on Jul. 6, 2016, the entire content of which is incorporated herein by reference.

TECHNICAL FIELD

The disclosure herein relates to a hemostatic device used for performing hemostasis by compressing a punctured site.

BACKGROUND DISCUSSION

In recent years, percutaneous treatment and examination have been performed in which a blood vessel in the arms or legs is punctured and an introducer sheath is introduced into a puncture site so as to deliver a medical device such as a catheter to a lesion area via a lumen of the introducer sheath. In a case where these treatments and examinations are performed, an operator needs to perform hemostasis at the puncture site after the introducer sheath is removed therefrom. In order to perform hemostasis, a known hemostatic device is used which includes a band for being wrapped around a limb such as the arms and legs, securing means for securing the band in a state where the band is wrapped around the limb, and an inflation portion that interlocks with the band, and that is inflated by injecting a fluid so as to compress the puncture site.

When this hemostatic device is used, a physician or a nurse generally connects a dedicated instrument such as a syringe separated from the hemostatic device to a port communicating with the inflation portion of the hemostatic device, and injects a fluid into the inflation portion by using the dedicated instrument, thereby inflating the inflation portion of the hemostatic device.

In contrast, according to the hemostatic device disclosed in JP-T-2014-521368, an injection portion (pressurization pump) which can inject gas into the inflation portion is attached to the hemostatic device. Specifically, the injection portion has an accommodation space which can accommodate the gas and a hole portion which communicates with the accommodation space in order to convey the gas. If the injection portion is pressed down (contracted) in a state where the hole portion is closed by a finger, the gas accommodated inside the injection portion is injected into the inflation portion. The inflation portion can be inflated by the injection portion attached to the inflation portion. Accordingly, the physician or the nurse can save time and effort by not having to carry the separate dedicated instrument, or can save time and effort by not having to connect the separate dedicated instrument to the hemostatic device. In addition, it is possible to prevent a disadvantage that the fluid cannot be injected into the inflation portion after the dedicated instrument is lost.

In a case where the injection portion is integrally provided, as in the hemostatic device disclosed in JP-T-2014-521368, a configuration of the injection portion can employ various forms. However, from a viewpoint of convenient pressing (operability) when the injection work is carried out or increasing a feeding amount of the gas so that the inflation portion can be quickly inflated, the injection portion needs to internally have a space which can accommodate a predetermined volume of the gas.

However, if the internal space of the injection portion is formed to be larger to some extent, the injection portion is disposed so as to protrude from the hemostatic device, thereby causing a possibility that the hole portion formed in the injection portion may be likely to come into contact with surrounding articles, or that a patient may inadvertently close the hole portion. If the injection portion is pressed down and contracted in a state where the hole portion is unintentionally closed in this way, the fluid is injected into the inflation portion, thereby causing a possibility that the puncture site may be compressed more than necessary.

SUMMARY

The disclosure herein provides a hemostatic device which can inflate an inflation portion without using a separate dedicated instrument, and which can prevent a hemostasis-requiring site from being unintentionally compressed more than necessary.

The hemostatic device according to the disclosure includes a band for being wrapped around a hemostasis-requiring site of a limb, securing means for securing the band in a state where the band is wrapped around the limb, an inflation portion that interlocks with the band, and that is inflated by injecting gas, and an injection portion that can inject gas into the inflation portion. The injection portion is disposed in the band, and is foldable so as to decrease a space formed inside the injection portion.

According to the hemostatic device configured as described above, the gas is injected into the inflation portion by the injection portion which communicates with the inflation portion. Therefore, without using a separate dedicated instrument, a physician or a nurse can dilate the inflation portion. In addition, the injection portion is foldable so as to decrease the space formed inside the injection portion after the inflation portion is inflated. Since the injection portion is folded, there is a low possibility that the injection portion may be further pressed down and the gas may be further injected into the inflation portion. Accordingly, the hemostatic device according to the disclosure here can suitably prevent the hemostasis-requiring site from being compressed more than necessary.

BRIEF DESCRIPTION OF THE DRAWINGS

FIG. 6(A) is a view illustrating a state before the injection portion is folded, and FIG. 6(B) is a view illustrating a state after the injection portion is folded.

FIG. 7(A) is a view illustrating a state where air is injected into an inflation portion, and FIG. 7(B) is a view illustrating a state where the inflation portion is completely inflated.

DETAILED DESCRIPTION

Figure 1:
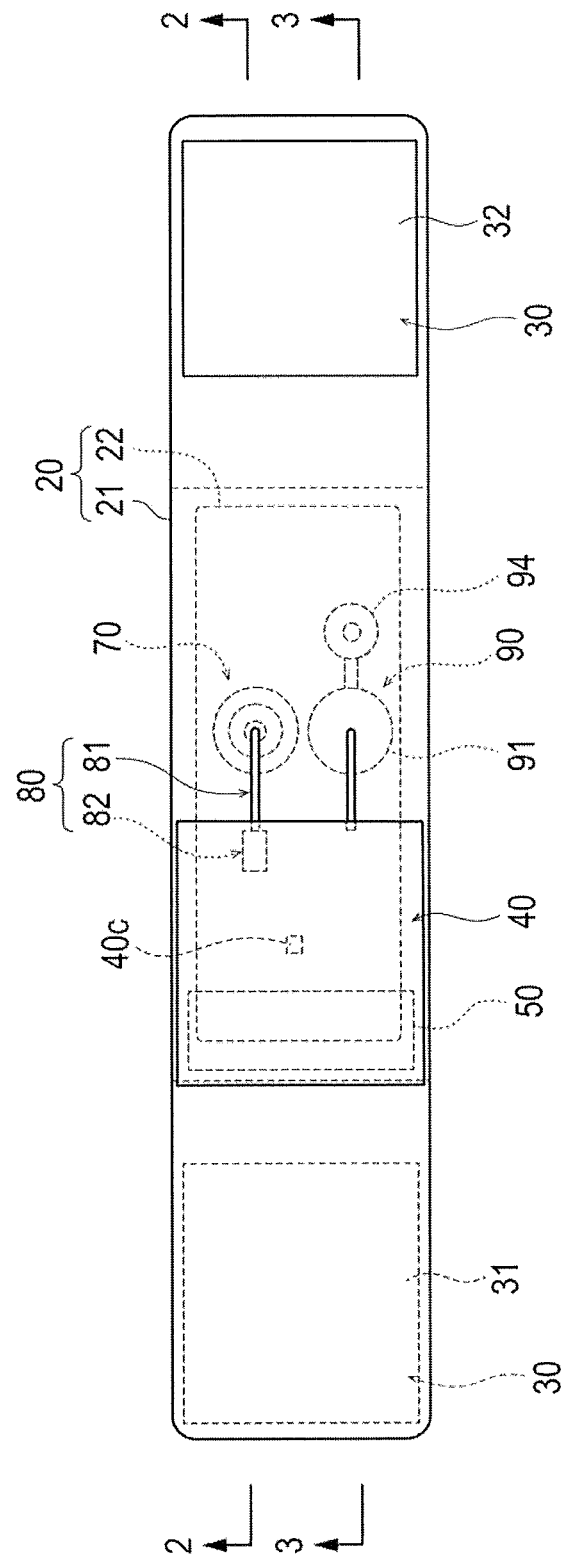
FIG. 1 is a plan view when a hemostatic device according to an exemplary embodiment of the disclosure is viewed from an inner surface side.

Hereinafter, an exemplary embodiment of the disclosure and modified examples thereof will be described with reference to the accompanying drawings. Note that, the following description does not limit the technical scope or the meaning of terms described in the appended claims. In addition, dimensional proportions in the drawings are exaggerated and may be different from actual proportions for convenience of description, in some cases.

Hereinafter, a hemostatic device 10 according to the exemplary embodiment of the disclosure will be described with reference to FIGS. 1 to 12. FIGS. 1 to 7 are views for describing each portion of the hemostatic device 10. FIGS. 8 to 12 are views for describing an example of using the hemostatic device 10.

Figure 8:
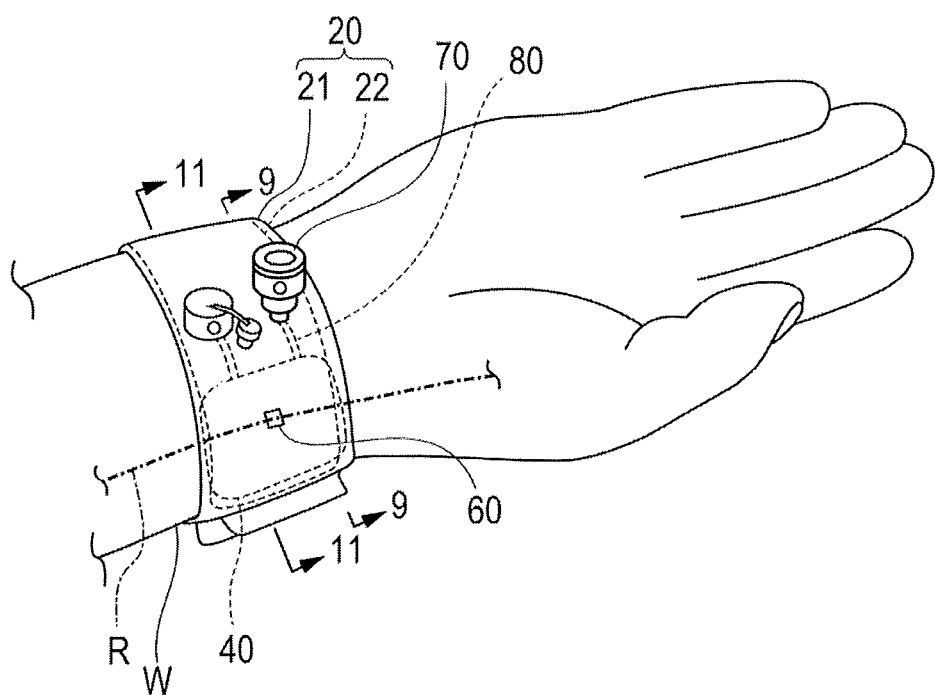
FIG. 8 is a schematic perspective view illustrating a state where the hemostatic device according to the exemplary embodiment is worn on a wrist.
Figure 10:
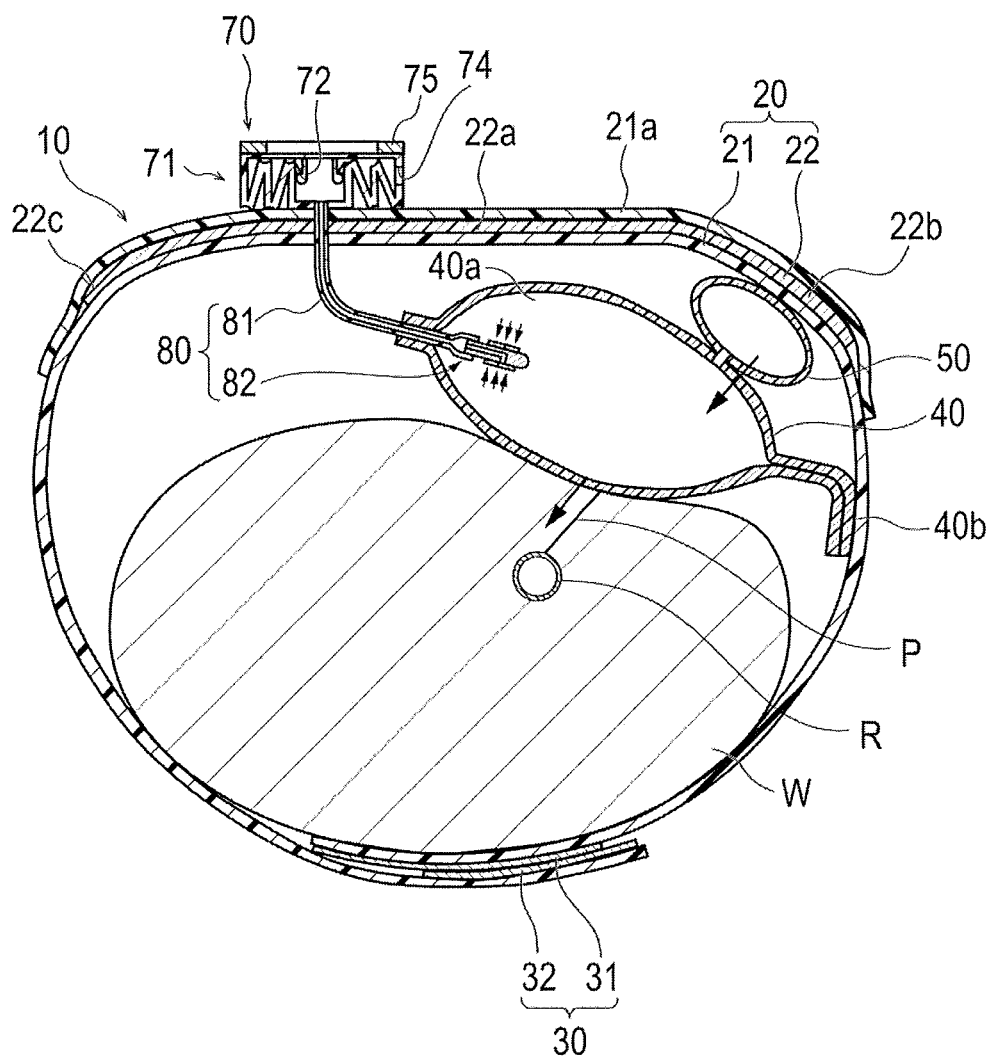
FIG. 10 is a sectional view taken along line 9-9 in FIG. 8, and is a view illustrating a state where the inflation portion is completely inflated.

As illustrated in FIGS. 8 and 10, the hemostatic device 10 according to the exemplary embodiment of the disclosure herein is used for performing hemostasis on a puncture site P (corresponding to a "hemostasis-requiring site") formed in a radial artery R of a wrist W (corresponding to a "limb") in order to insert a catheter for performing treatment and examination into a blood vessel, after an introducer sheath indwelling the puncture site P is removed.

Figure 2:
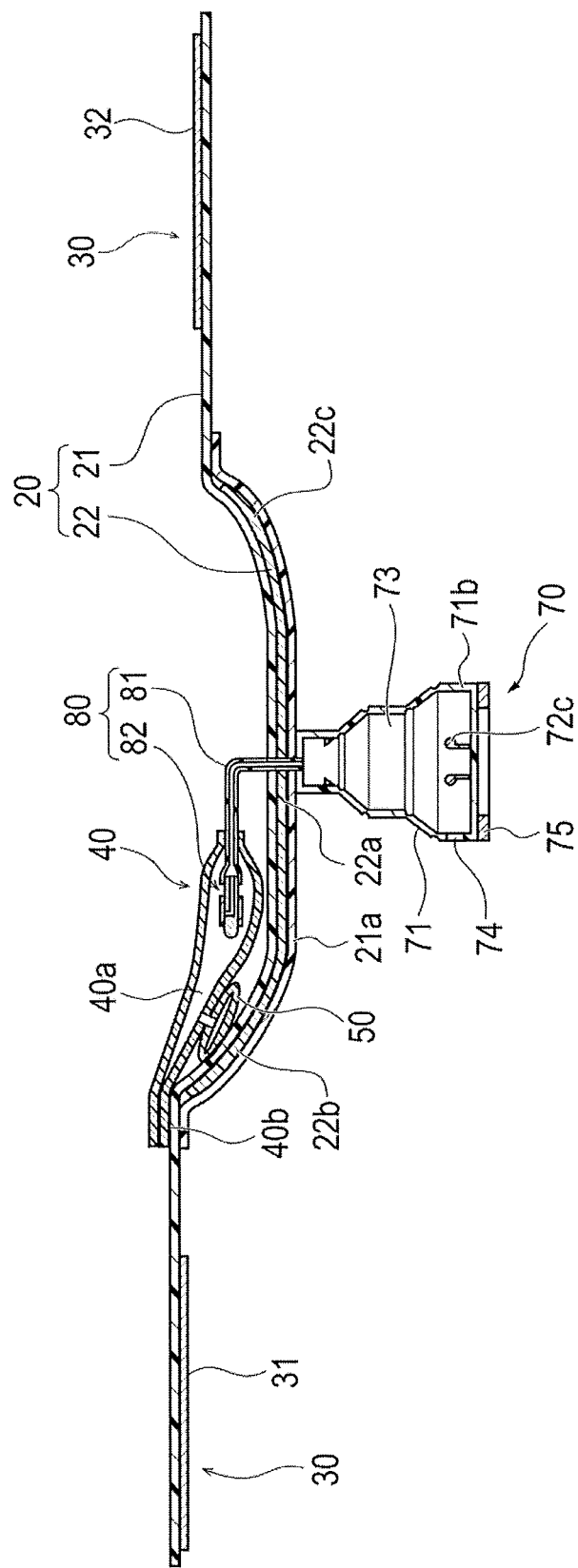
FIG. 2 is a sectional view taken along line 2-2 in FIG. 1.
Figure 3:
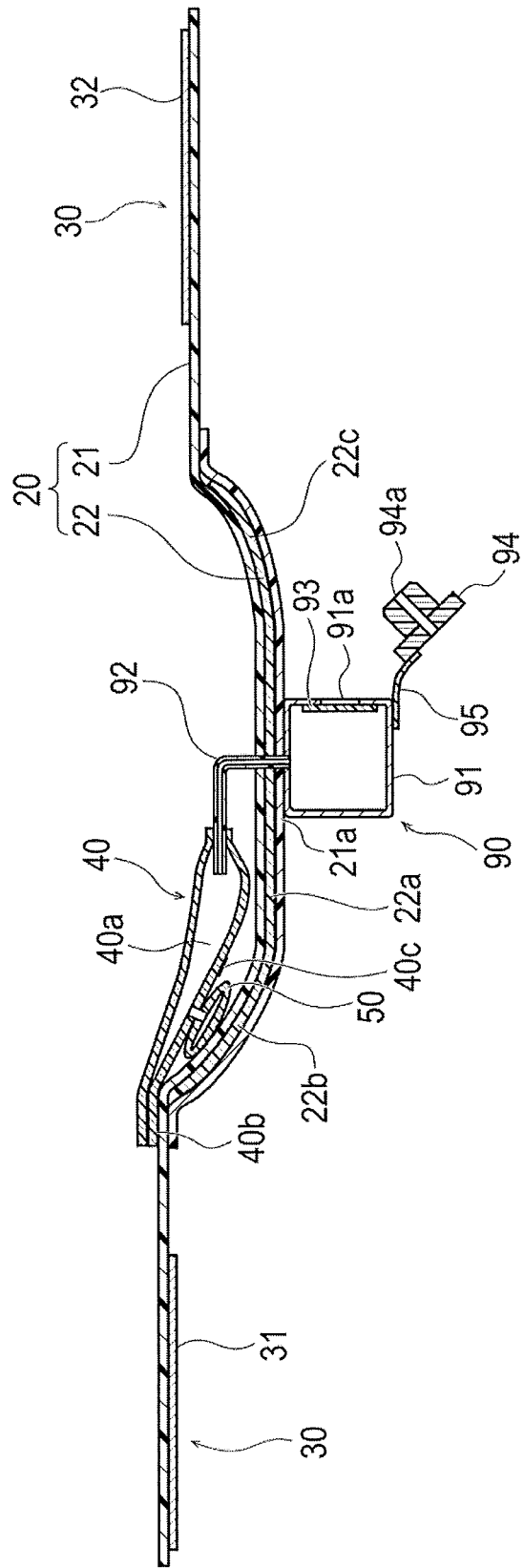
FIG. 3 is a sectional view taken along line 3-3 in FIG. 1.

As illustrated in FIGS. 1 to 3, the hemostatic device 10 has a band 20 for being wrapped around the wrist W, a surface fastener 30 (corresponding to "securing means") for securing the band 20 in a state where the band 20 is wrapped around the wrist W, an inflation portion 40 that is inflated by injecting air (corresponding to "gas"), and that compresses the puncture site P, an auxiliary compression portion 50 that is disposed between the inflation portion 40 and the band 20, a marker 40c for aligning the inflation portion 40 with the puncture site P, an injection portion 70 that can inject the air into the inflation portion 40 and the auxiliary compression portion 50, a circulation channel 80 that causes the inflation portion 40 and the injection portion 70 to communicate with each other, and a discharge portion 90 that discharges the air contained inside the inflation portion 40 outward.

Note that, in the description herein, when the band 20 is in a state of being wrapped around the wrist W, a surface (wearing surface) on a side facing a body surface of the wrist W is referred to as an "inner surface" (corresponding to a "first surface"), and a surface opposite thereto is referred to as an "outer surface" (corresponding to a "second surface").

The band 20 includes a belt 21 configured to include a flexible belt-like member, and a support plate 22 which is more rigid than the belt 21.

Figure 9:
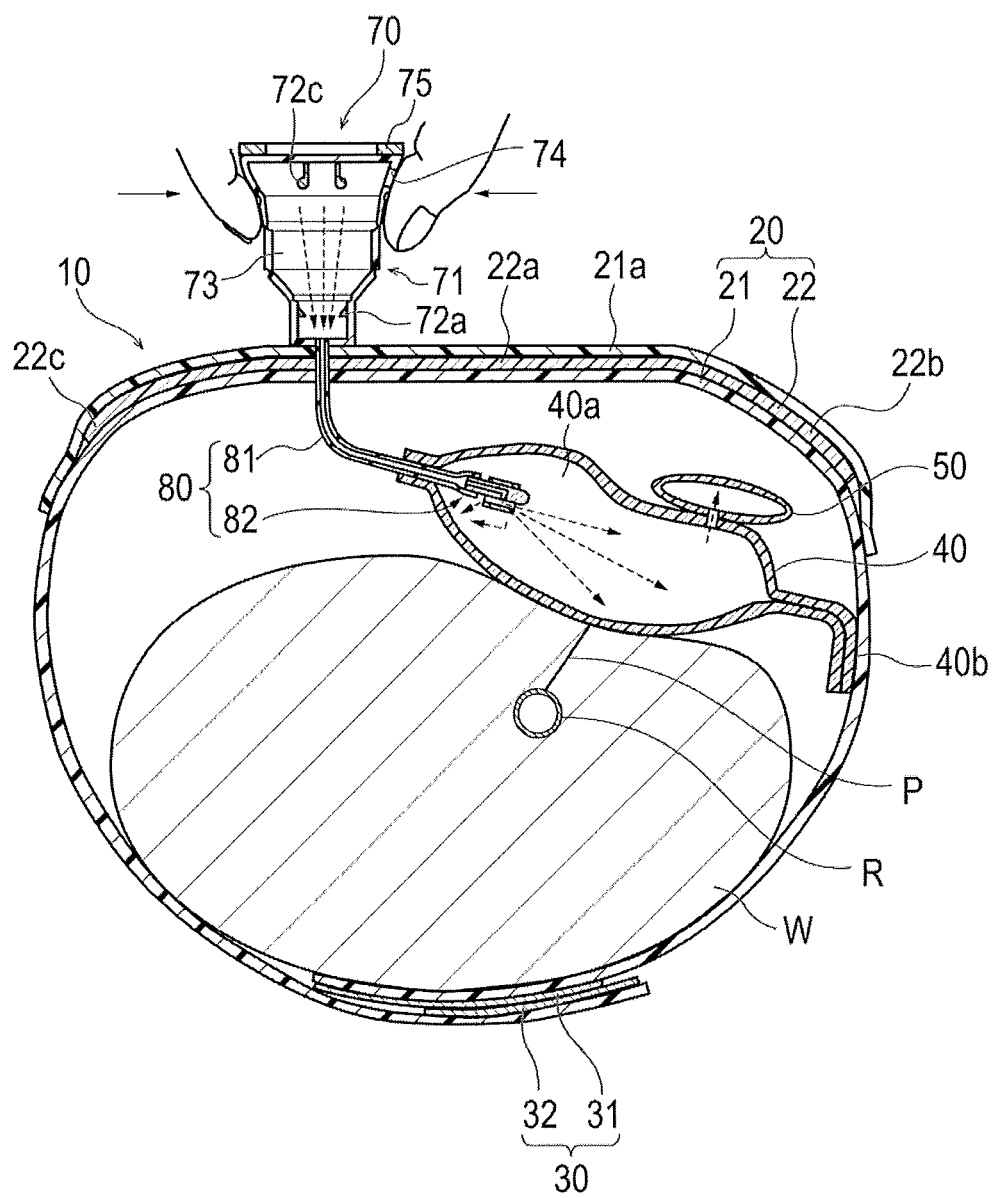
FIG. 9 is a sectional view taken along line 9-9 in FIG. 8, and is a view illustrating a state where the inflation portion is inflated.

As illustrated in FIGS. 8 and 9, the belt 21 is wrapped substantially one time around an outer periphery of the wrist W. As illustrated in FIG. 2, a support plate holder 21a for holding the support plate 22 is formed in a central portion of the belt 21. The support plate holder 21a is adapted to have a double layer construction in such a way that a separate belt-like member is joined to the outer surface side (or the inner surface side) by means of fusion bonding (heat-welding, high frequency fusion, or ultrasound fusion) or adhesion (adhesion using an adhesive or a solvent), thereby holding the support plate 22 inserted into a gap or pocket formed between the double layer structure.

A male side (or a female side) 31 of the surface fastener 30, such as a hook and loop fastener (e.g., a product commonly known as VELCRO® or Magic Tape in Japan, is disposed on the outer surface side of a portion in the vicinity of the left end in FIG. 1 of the belt 21, and a female side (or a male side) 32 of the surface fastener 30 is disposed on the inner surface side of a portion in the vicinity of the right end in FIG. 1 of the belt 21. As illustrated in FIG. 9, the belt 21 is wrapped around the wrist W, and the male side 31 and the female side 32 are joined to each other. In this manner, the band 20 is worn on the wrist W. Note that, without being limited to the surface fastener 30, means for securing the band 20 in a state where the band 20 is wrapped around the wrist W may be a snap, a button, a clip, or a frame member passing through the end portion of the belt 21, for example.

A configuration material of the belt 21 is not particularly limited as long as the material is flexible. For example, these materials include polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any optional combination thereof (blend resin, polymer alloy, and laminate).

In addition, it is preferable that a portion overlapping at least the inflation portion 40 in the belt 21 is substantially transparent. However, without being limited to transparency, the portion may be translucent or colored transparent. In this manner, the puncture site P is visible from the outer surface side, thereby enabling the marker 40c (to be described later) to easily align with the puncture site P.

As illustrated in FIG. 2, the support plate 22 is inserted between the support plate holder 21a formed to have the double layer structure of the belt 21. In this manner, the support plate 22 is held by the belt 21. The support plate 22 has a plate shape in which at least a portion thereof is curved toward the inner surface side (wearing surface side). The support plate 22 is configured to include a material which is more rigid than that of the belt 21, and is adapted to maintain a substantially constant shape. The method of providing the support plate 22 in or on the belt 21 is not limited to the illustrated arrangement, and may involve joining the support plate 22 to the inner surface side or the outer surface side of the band 20 by a suitable method such as welding or adhesion. Also, another acceptable arrangement is one in which the belt 21 is connected to both ends of the support plate 22. It is thus not necessary for a portion of the belt 21 to overlap with the support plate 22.

The support plate 22 has a long shape in the longitudinal direction of the belt 21. A central portion 22a in the longitudinal direction of the support plate 22 is hardly curved, and has a flat plate or generally planar shape. Both sides of the central portion 22a respectively have a first curved portion 22b (left side in FIG. 2) and a second curved portion 22c (right side in FIG. 2) which are curved toward the inner peripheral side and along the longitudinal direction (circumferential direction of the wrist W) of the belt 21.

By way of example, configuration materials of the support plate 22 include acrylic resin, polyvinyl chloride (particularly, rigid polyvinyl chloride), polyethylene, polypropylene, polyolefin such as polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET), polyester such as polybutylene terephthalate (PBT), butadiene-styrene copolymer, aromatic or aliphatic polyamide, and fluorine-based resin such as polytetrafluoroethylene.

Similar to the belt 21, it is preferable that a portion of the support plate 22 overlapping the inflation portion 40 is substantially transparent. However, without being limited to transparency, the portion may be translucent or colored transparent. In this manner, the puncture site P is reliably visible from the outer surface side, thereby enabling the marker 40c (to be described later) to easily align with the puncture site P. Note that, the support plate 22 may not have a portion which is substantially flat or planar like the central portion 22a, that is, the support plate 22 may be curved over the entire length.

The inflation portion 40 is provided with a function to apply a compressing force to the puncture site P after being inflated by injecting the air. According to the exemplary embodiment, as illustrated in FIGS. 1 and 2, the inflation portion 40 is configured to include a bag-like member obtained in such a way that peripheral edges are bonded or fused by overlapping two substantially rectangular sheets with each other. In this manner, an inflation space 40a is formed between the two sheets. Note that, a configuration of the inflation portion 40 is not particularly limited as long as the inflation portion 40 can be dilated by injecting the air. For example, the inflation portion 40 may be configured to include a bag-like member obtained in such a way that edge portions are bonded or fused by folding one sheet, or may be configured to include a balloon-like member which does not include the edge portion. In addition, an outer shape of the inflation portion 40 is not particularly limited. For example, in a state where the inflation portion 40 is not inflated, the inflation portion 40 may be provided with the outer shapes such as circular, elliptical, and polygonal shapes in a plan view.

As illustrated in FIG. 2, the inflation portion 40 is disposed so as to overlap the vicinity between the first curved portion 22b and the central portion 22a of the support plate 22. Therefore, as illustrated in FIG. 10, when the inflation portion 40 is inflated, the belt 21 and the support plate 22 restrain the inflation portion 40 from being inflated in a direction separated from the body surface of the wrist W, thereby concentrating the compressing force of the inflation portion 40 on the wrist W side. Therefore, the puncture site P can be suitably compressed.

In addition, the inflation portion 40 is attached to the belt 21 of the band 20 via a flexible holding portion 40b. Note that, according to the exemplary embodiment, the holding portion 40b is configured to include an edge portion on a side having the male side 31 of the surface fastener in the inflation portion 40. However, the holding portion 40b may be configured to include a member separated from the inflation portion 40. In addition, a position for disposing the holding portion 40b in the inflation portion 40 and a position for attaching the holding portion 40b to the band 20 are not particularly limited as long as the inflation portion 40 can interlock with the band 20.

A configuration material of the inflation portion 40 is not particularly limited as long as the material is flexible. For example, it is possible to use the same configuration material as that of the above-described band 20. In addition, it is preferable that the inflation portion 40 is configured to include a thermoplastic material which is the same material or the same type as that of the band 20. In this manner, the inflation portion 40 can be easily joined with the band 20 by means of fusion bonding, and the hemostatic device 10 can be easily manufactured.

It is preferable that the inflation portion 40 is substantially transparent. However, without being limited to transparency, the inflation portion 40 may be translucent or colored transparent. In this manner, the puncture site P is visible from the outer surface side, thereby enabling the marker 40c (to be described later) to easily align with the puncture site P.

The auxiliary compression portion 50 is provided to press the inflation portion 40 as illustrated by an arrow in FIG. 10 so as to adjust a direction of the compressing force applied to the puncture site P by the inflation portion 40.

Similar to the inflation portion 40, the auxiliary compression portion 50 is configured to include a bag-like member. Note that, the auxiliary compression portion 50 may be configured to include a sponge-like substance, an elastic material, an aggregate of fibers such as cotton, or a combination thereof, for example.

The auxiliary compression portion 50 is attached to the inflation portion 40 so that an internal space thereof communicates with the inflation space 40a of the inflation portion 40. Therefore, if the air is injected into the inflation portion 40, the auxiliary compression portion 50 is also inflated.

As illustrated in FIG. 3, the marker 40c is disposed at substantially a center of the inflation portion 40 on a side facing the band 20. Since this marker 40c is disposed in the inflation portion 40, the inflation portion 40 can easily align with the puncture site P. Accordingly, misalignment of the inflation portion 40 is restrained. Note that, the marker 40c may be disposed on a side facing the wrist W in the inflation portion 40. In this case, it is preferable that the marker 40c is disposed on an inner surface inside the inflation portion 40 so as not to directly come into contact with the puncture site P.

Without being particularly limited, a shape of the marker 40c includes circular, triangular, and square shapes, for example. In the exemplary embodiment, the marker 40c has the square shape.

A size of the marker 40c is not particularly limited. However, for example, in a case where the shape of the marker 40c is the square shape, it is preferable that one side length thereof is in a range of 1 to 4 mm. If one side length is 5 mm or longer, the size of the marker 40c is larger than the size of the puncture site P. Consequently, the central portion of the inflation portion 40 is less likely to align with the puncture site P.

Without being particularly limited, a material of the marker 40c includes oily colorants such as ink, and resins kneaded with pigments.

A color of the marker 40c is not particularly limited as long as the color enables the inflation portion 40 to align with the puncture site P. However, it is preferable that the color is a green color system. If the green color system is used, the marker 40c is easily visible on the blood or the skin. Accordingly, the inflation portion 40 is much likely to align with the puncture site P.

In addition, it is preferable that the marker 40c is translucent or colored transparent. In this manner, the puncture site P is visible from the outer surface side of the marker 40c.

A method of disposing the marker 40c in the inflation portion 40 is not particularly limited. However, for example, the method includes a method of printing the marker 40c on the inflation portion 40, a method of fusing the marker 40c to the inflation portion 40, and a method of attaching the marker 40c to the inflation portion 40 by applying an adhesive to one side surface of the marker 40c.

Figure 4:
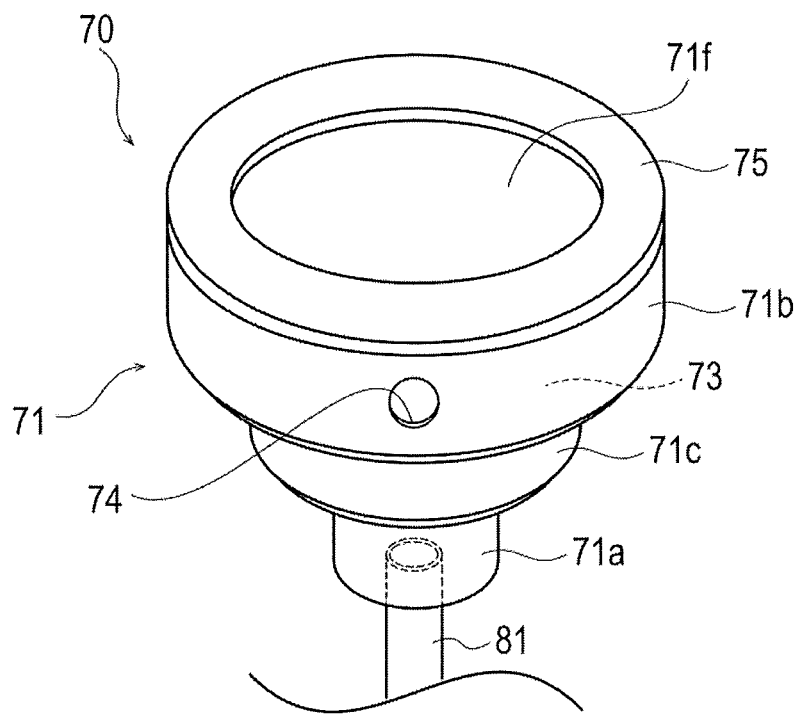
FIG. 4 is a schematic perspective view illustrating an injection portion of the hemostatic device according to the exemplary embodiment.

The injection portion 70 is provided to inject air into the inflation portion 40. As illustrated in FIGS. 2 and 4, the injection portion 70 is configured to include a three-dimensional member including an accommodation space 73 which can accommodate the air to be injected. Note that, the injection portion 70 is disposed on the band 20. However, FIG. 4 illustrates the injection portion 70 by omitting the band 20.

The injection portion 70 is disposed on the outer surface side of the band 20. Therefore, compared to a case where the injection portion 70 is disposed so as to protrude towards the wrist W side from the band 20, the injection portion 70 is less likely to come into contact with the wrist W of the wearer. Accordingly, it is possible to reduce discomfort felt by the wearer. In addition, particularly in the exemplary embodiment, the injection portion 70 does not overlap the inflation portion 40 in the band 20 as illustrated in FIG. 2, and is instead disposed at a position overlapping the support plate 22. That is, a cross section perpendicular to the longitudinal direction of the band 20 at a position on the band 20 of the injection portion 70 does not include the inflation portion 40, but includes the support plate 22. Therefore, even if the injection portion 70 is disposed on the band 20, the alignment of the inflation portion 40 with the puncture site P is not hindered, and the injection operation for injecting the air into the inflation portion 40 on the very rigid support plate 22 can be performed, thereby facilitating the injection operation. Note that, a position of the injection portion 70 is not particularly limited as long as the injection portion 70 is disposed on the band 20.

Figure 6A:
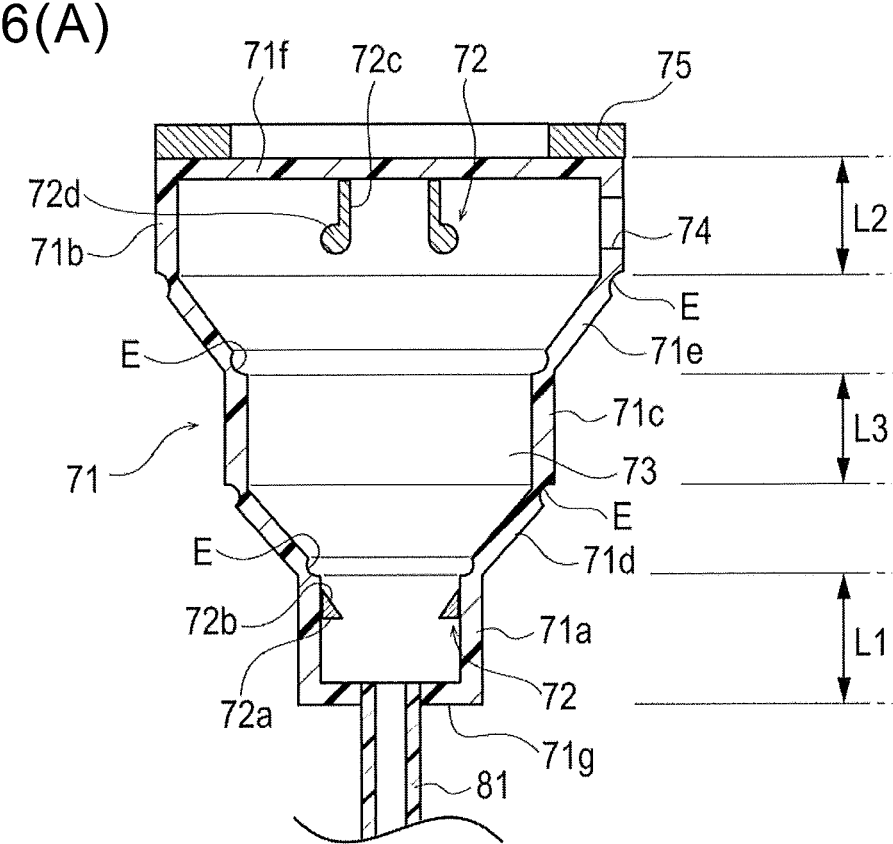
FIGS. 6(A)-6(B) are schematic sectional views illustrating the injection portion.

As illustrated in FIGS. 2, 4, and 6(A) and (B), the injection portion 70 has a vertical wall portion 71 configured to be foldable, a securing mechanism 72 for securing the vertical wall portion 71 in a folded state, an accommodation space 73 which can accommodate the air, a hole portion 74 which causes the accommodation space 73 to communicate with the outside, and a rigid portion 75 which is much less likely to be deformed than other portions of the injection portion 70.

The vertical wall portion 71 includes a link mechanism configured to be foldable. As illustrated in FIG. 6(A), the vertical wall portion 71 has a first side surface 71a, a second side surface 71b, a third side surface 71c, a first interlock portion 71d which interlocks the first side surface 71a and the third side surface 71c with each other, and a second interlock portion 71e which interlocks the second side surface 71b and the third side surface 71c with each other.

Among the plurality of side surfaces 71a, 71b, and 71c, the first side surface 71a is disposed at a position closest to the band 20 side.

Figure 6B:
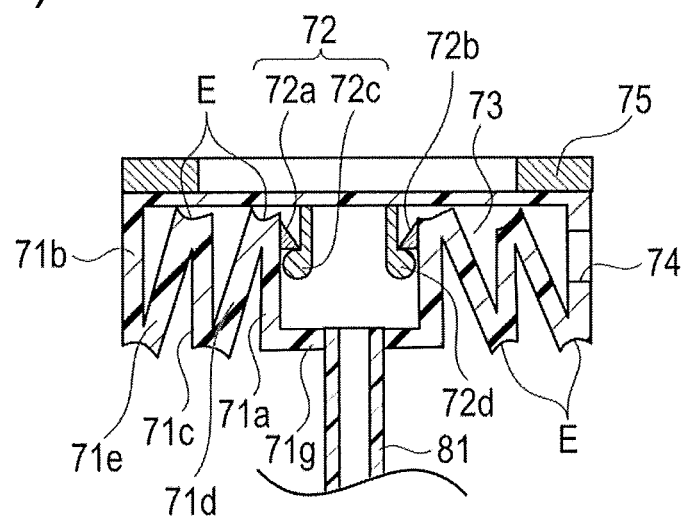

Among the plurality of side surfaces 71a, 71b, and 71c, the second side surface 71b is disposed at a position farthest away from the band 20 side. The second side surface 71b has an inner periphery and an outer periphery which are larger than those of the first side surface 71a. As illustrated in FIG. 6(B), in a state where the vertical wall portion 71 is folded, the second side surface 71b covers the outer periphery of both the first side surface 71a and the third side surface 71c.

The third side surface 71c is disposed between the first side surface 71a and the second side surface 71b. The third side surface 71c is configured to have an inner periphery and an outer periphery which are larger than those of the first side surface 71a, and is configured to have the inner periphery and the outer periphery being smaller than those of the second side surface 71b. As illustrated in FIG. 6(B), in a state where the vertical wall portion 71 is folded, the third side surface 71c covers the outer periphery of the first side surface 71a.

The first interlock portion 71d interlocks the first side surface 71a and the third side surface 71c with each other. The first interlock portion 71d is configured to be tilted or angled between the first side surface 71a and the third side surface 71c, in a state where the vertical wall portion 71 is unfolded. Therefore, when the vertical wall portion 71 is folded, the vertical wall portion 71 can be easily folded.

The second interlock portion 71e interlocks the second side surface 71b and the third side surface 71c with each other. The second interlock portion 71e is configured to be tilted or angled between the second side surface 71b and the third side surface 71c, in a state where the vertical wall portion 71 is unfolded. Therefore, when the vertical wall portion 71 is folded, the vertical wall portion 71 can be easily folded.

As illustrated in FIG. 6(A) of the exemplary embodiment, a notch E is recessed inward and formed on an inner peripheral surface of a connection location between the first side surface 71a and the first interlock portion 71d, an outer peripheral surface of a connection location between the first interlock portion 71d and the third side surface 71c, an inner peripheral surface of a connection location between the third side surface 71c and the second interlock portion 71e, and an outer peripheral surface of a connection location between the second interlock portion 71e and the second side surface 71b. Since the notch E is formed in this way, the vertical wall portion 71 can be easily bent and folded. Note however, that the notch E may not necessarily be provided.

It is preferable that a length L1 along the vertical direction of the first side surface 71a in FIG. 6, a length L2 along the vertical direction of the second side surface 71b in FIG. 6, and a length L3 along the vertical direction of the third side surface 71c in FIG. 6(A) satisfy L2≥L3≥L1. According to this configuration, in a state where the vertical wall portion 71 is folded as illustrated in FIG. 6(B), a height of the second side surface 71b can become higher than each height of the first side surface 71a and the third side surface 71c. Therefore, in a state where the vertical wall portion 71 is folded, the first side surface 71a and the third side surface 71c can be prevented from projecting downward after crossing the second side surface 71b, and can be prevented from inadvertently coming into contact with the surroundings.

It is preferable that the vertical wall portion 71 can be contracted. For example, in order that the vertical wall portion 71 can return to the original expanded position after being contracted, it is preferable that the vertical wall portion 71 is configured to include an elastomer material such as silicone rubber or latex rubber, a thermoplastic material such as polypropylene and polyethylene, or various thermoplastic elastomer materials having both properties.

As illustrated in FIGS. 6(A) and 6(B), the securing mechanism 72 has a first securing portion 72a attached to the inner periphery of the first side surface 71a, and a second securing portion 72c attached to the lower side (accommodation space 73 side) of an upper surface portion 71f formed upward so as to cover the second side surface 71b.

As illustrated in FIGS. 6(A) and 6(B), the first securing portion 72a has a tapered portion 72b which is disposed so that the inner diameter decreases downward (toward the tube 81 side).

As illustrated in FIGS. 6(A) and 6(B), the second securing portion 72c includes a protruding portion 72d protruding outward on the lower side (tube 81 side).

According to the securing mechanism 72 configured as described above, since the vertical wall portion 71 is folded, the first securing portion 72a and the second securing portion 72c are secured by engaging with each other as illustrated in FIG. 6(B). Therefore, in a state where the vertical wall portion 71 is folded, it is possible to prevent the vertical wall portion 71 from being unintentionally brought into an unfolded state.

Note that, the securing mechanism 72 is not limited to the above-described configuration as long as the configuration can maintain the folded state of the vertical wall portion 71.

It is preferable that a material configuring the first securing portion 72a and the second securing portion 72c is a material which is more rigid than that of the vertical wall portion 71. For example, this material includes a known metal material or a plastic material.

The accommodation space 73 is formed inside the vertical wall portion 71. It is preferable that a volume of the accommodation space 73 is approximately ¼ to ⅓ of a volume of the inflation space 40a in the inflation portion 40. In this manner, the injection portion 70 can be formed to have a proper size. The injection portion 70 can be prevented from hindering a manual skill demonstrated around the hemostatic device 10, and it is possible to reduce the number of injection operations for injecting the air into the inflation portion 40 (to be described later).

As illustrated in FIGS. 6(A) and 6(B), the hole portion 74 is disposed by penetrating the second side surface 71b along a direction orthogonal to the second side surface 71b.

For example, as illustrated in FIG. 9, in a state where a physician or a nurse grips the injection portion 70 with his or her thumb and forefinger and closes the hole portion 74, the thumb and the forefinger are moved close to each other, and the injection portion 70 is pressed down and deformed. In this manner, the air contained inside the accommodation space 73 can be injected into the inflation portion 40.

If the operation for pressing down the injection portion 70 is performed as described above, the air is delivered to the inflation portion 40 by way of the tube 81. In a case where the operation for delivering the air to the inflation portion 40 is performed again, the fingers are separated from the hole portion 74, and the accommodation space 73 is brought into a state of communicating with the outside. The injection portion 70 is deformed so as to restore the initial shape illustrated in FIG. 9 by the air being conveyed to the accommodation space 73 through the hole portion 74. If the injection portion 70 is pressed down again in a state where the air has been conveyed into the accommodation space 73, the air can again be delivered to the inflation portion 40.

When the inflation portion 40 is inflated, a pressing force for pressing down the injection portion 70 while closing the hole portion 74 with the finger is applied in a direction intersecting the extending direction (vertical direction in FIG. 6(A)) of the injection portion 70. Therefore, the pressing force is relatively less likely to be transmitted to the puncture site P. It is thus possible to suitably prevent a disadvantage that the puncture site P is compressed more than necessary by the injection operation for injecting the air into the inflation portion 40. In addition, the pressing force for pressing down the injection portion 70 while closing the hole portion 74 with the finger is relatively less likely to be transmitted to the puncture site P. Accordingly, when the inflation portion 40 is inflated, a wearer can relatively accurately recognize only the compressing force applied to the puncture site P by the inflation portion 40. Therefore, based on the compressing force felt by the wearer, the air can be injected into the inflation portion 40 can be the optimum amount for performing hemostasis on the puncture site P. Furthermore, the hole portion 74 is formed in the vertical wall portion 71. Accordingly, the hole portion 74 is less likely to be closed by a patient's finger or surrounding articles. There is thus a low possibility that the air is unintentionally injected into the inflation portion 40 from the injection portion 70.

Note that, the number of hole portions 74 is not particularly limited as long as the number is one or more. In addition, a shape of the hole portion 74 is not limited to the illustrated case. In addition, it is preferable to form the hole portion 74 so that the hole portion 74 penetrates the injection portion 70 in a direction intersecting the extending direction of the injection portion 70. However, for example, the hole portion 74 can also be formed in the upper surface portion 71f.

As illustrated in FIGS. 6(A) and 6(B), the rigid portion 75 is disposed above the upper surface portion 71f, and is fixed to the vertical wall portion 71. A method of securing the rigid portion 75 and the vertical wall portion 71 to each other is not particularly limited. However, for example, the method includes adhesion using an adhesive. In the exemplary embodiment, the rigid portion 75 is configured to have a hollow ring shape.

A material for configuring the rigid portion 75 is not particularly limited as long as the material is much less likely to be deformed than the vertical wall portion 71 when the vertical wall portion 71 is folded. However, for example, the material includes a known metal material or a plastic material.

Since the rigid portion 75 is fixed to the upper portion of the vertical wall portion 71, when the vertical wall portion 71 is pressed and folded, a downward force can be uniformly applied to the upper surface portion 71f of the vertical wall portion 71. Therefore, the vertical wall portion 71 can be easily folded. Note that, when the vertical wall portion 71 is folded, the air contained inside the accommodation space 73 can be discharged outward via the hole portion 74. Accordingly, the vertical wall portion 71 can be smoothly folded.

Figure 5:
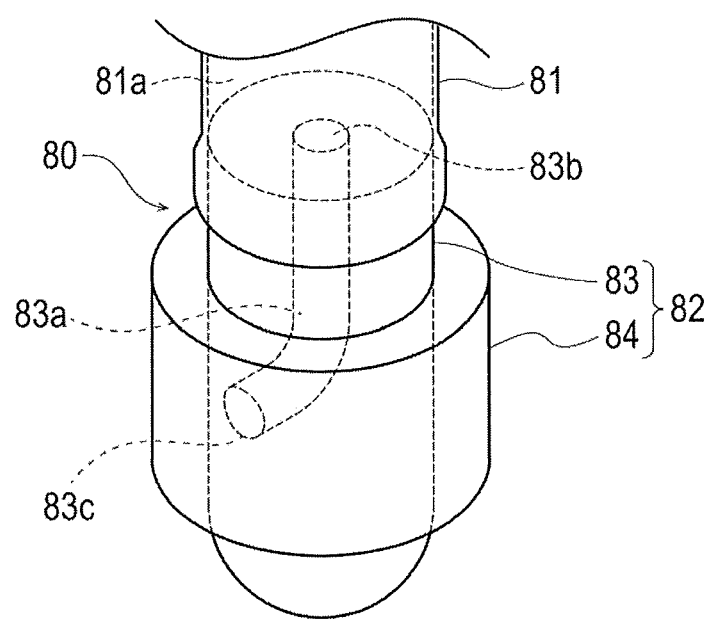
FIG. 5 is a schematic perspective view illustrating a circulation channel of the hemostatic device according to the exemplary embodiment.

As illustrated in FIGS. 2 and 5, the circulation channel 80 includes the tube 81 which causes the inflation space 40a of the inflation portion 40 and the accommodation space 73 of the injection portion 70 to communicate with each other, and a backflow prevention mechanism 82 which prevents the air from flowing out to the injection portion 70 from the inflation portion 40.

Figure 7A:
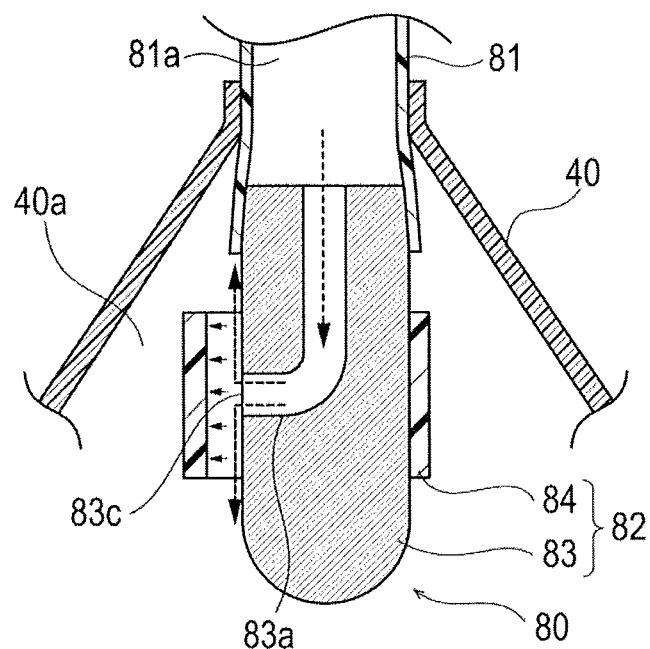
FIGS. 7(A)-7(B) are enlarged sectional views illustrating a backflow prevention mechanism of the hemostatic device according to the exemplary embodiment.
Figure 7B:
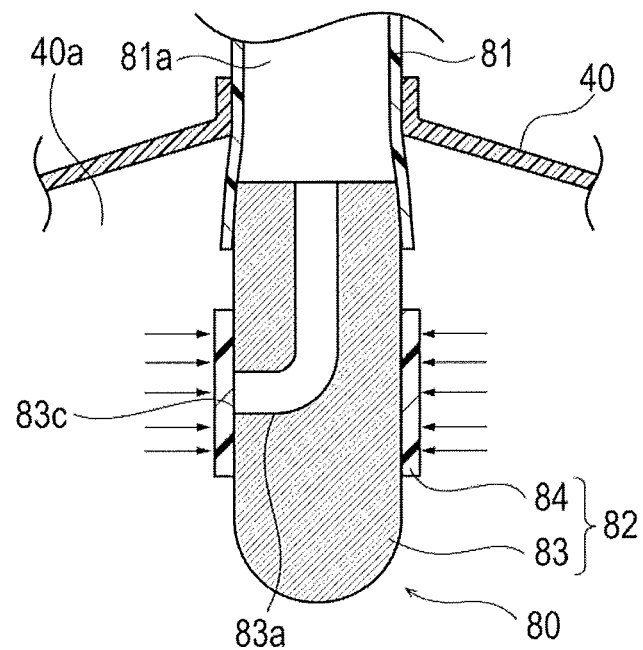

A proximal portion of the tube 81 is attached to a bottom surface portion 71g (refer to FIGS. 6(A) and 6(B)) of the injection portion 70, and a distal portion is attached to the inflation portion 40 so as to enter the inflation space 40a of the inflation portion 40 (refer to FIGS. 7(A) and 7(B)). Note that, a position for attaching the tube 81 in the injection portion 70 is not particularly limited as long as the accommodation space 73 of the injection portion 70 and the inflation space 40a of the inflation portion 40 can communicate with each other.

In addition, as illustrated in FIG. 2, a through-hole (not numbered) is provided in the band 20, and the tube 81 is disposed so as to be inserted into the through-hole. Note that, for example, without providing the through-hole in the band 20, the tube 81 may be disposed so as to wrap around the band 20.

The backflow prevention mechanism 82 is disposed inside the inflation portion 40. As illustrated in FIG. 5, the backflow prevention mechanism 82 includes a core member 83 connected to a distal portion of the tube 81 and a covering member 84 which covers the core member 83.

As illustrated in FIGS. 7(A) and 7(B), the core member 83 interlocks with the tube 81 in such a way that a proximal portion of the core member 83 is fixed by being inserted into a distal side of a lumen 81a of the tube 81.

The core member 83 is provided with a substantially columnar outer shape. The core member 83 has a proximal opening portion 83b which is open inside the lumen 81a of the tube 81 and a distal opening portion 83c which is open on a surface having the covering member 84 in the core member 83. The lumen 83a of the core member 83 communicates with the proximal opening portion 83b and the distal opening portion 83c.

Note that, the core member 83 and the tube 81 may interlock with each other using a form other than a method of inserting the proximal portion of the core member 83 into the lumen 81a of the tube 81 and securing the same. For example, the lumen 83a of the core member 83 and the lumen 81a of the tube 81 may be caused to hermetically communicate with each other by bonding both in a state where the proximal surface of the core member 83 and the distal surface of the tube 81 are caused to face each other.

It is preferable that a configuration material of the core member 83 is more rigid than that of the covering member 84. For example, the material includes a known metal material or a plastic material. Note that, from a viewpoint of pressure resistance, it is preferable that the core member 83 is formed of a metal material.

The covering member 84 is provided with a cylindrical outer shape. The core member 83 is inserted into the covering member 84.

It is preferable that a configuration material of the covering member 84 is an elastic member. For example, this material includes elastomer materials such as butyl rubber, polysulfide rubber, epichlorohydrin rubber, high nitrile rubber, fluororubber, and silicone rubber, and various thermoplastic elastomer materials.

The discharge portion 90 is provided to discharge the air contained inside the inflation portion 40 outward. As illustrated in FIG. 3, the discharge portion 90 includes a discharge port 91 disposed on the band 20, a tube 92 which causes the internal space of the discharge port 91 and the inflation space 40a of the inflation portion 40 to communicate with each other, a valve 93 which can prevent the air contained in the inflation portion 40 from being discharged outward, a switching member 94 which can switch on and off the communication between the internal space of the discharge port 91 and the outside, and an interlock member 95 which prevents the switching member 94 from being detached.

As illustrated in FIGS. 1 and 3, the discharge port 91 is provided with a columnar outer shape. However, without being particularly limited, the outer shape of the discharge port 91 may be a sphere or a polygonal prism such as a rectangular prism.

The discharge port 91 is disposed on the outer surface side of the band 20. Therefore, compared to a case where the discharge port 91 is disposed so as to protrude toward the wrist W side from the band 20, the discharge port 91 is less likely to come into contact with the wrist W of the wearer. Accordingly, it is possible to reduce discomfort felt by the wearer. In addition, particularly in the exemplary embodiment, the discharge port 91 does not overlap the inflation portion 40 on the outer surface side of the band 20, and is instead disposed at a position overlapping the support plate 22. That is, a cross section perpendicular to the longitudinal direction of the band 20 at a position on the band 20 of the discharge port 91 does not include the inflation portion 40, but includes the support plate 22. Therefore, even if the discharge port 91 is disposed on the band 20, the alignment of the inflation portion 40 with the puncture site P is not hindered, and the switching member 94 (to be described later) is attached to or detached from the discharge port 91 on the very rigid support plate 22, thereby facilitating the attaching or detaching operation of the switching member 94. However, a position for the discharge port 91 in the band 20 is not particularly limited.

Figure 12:
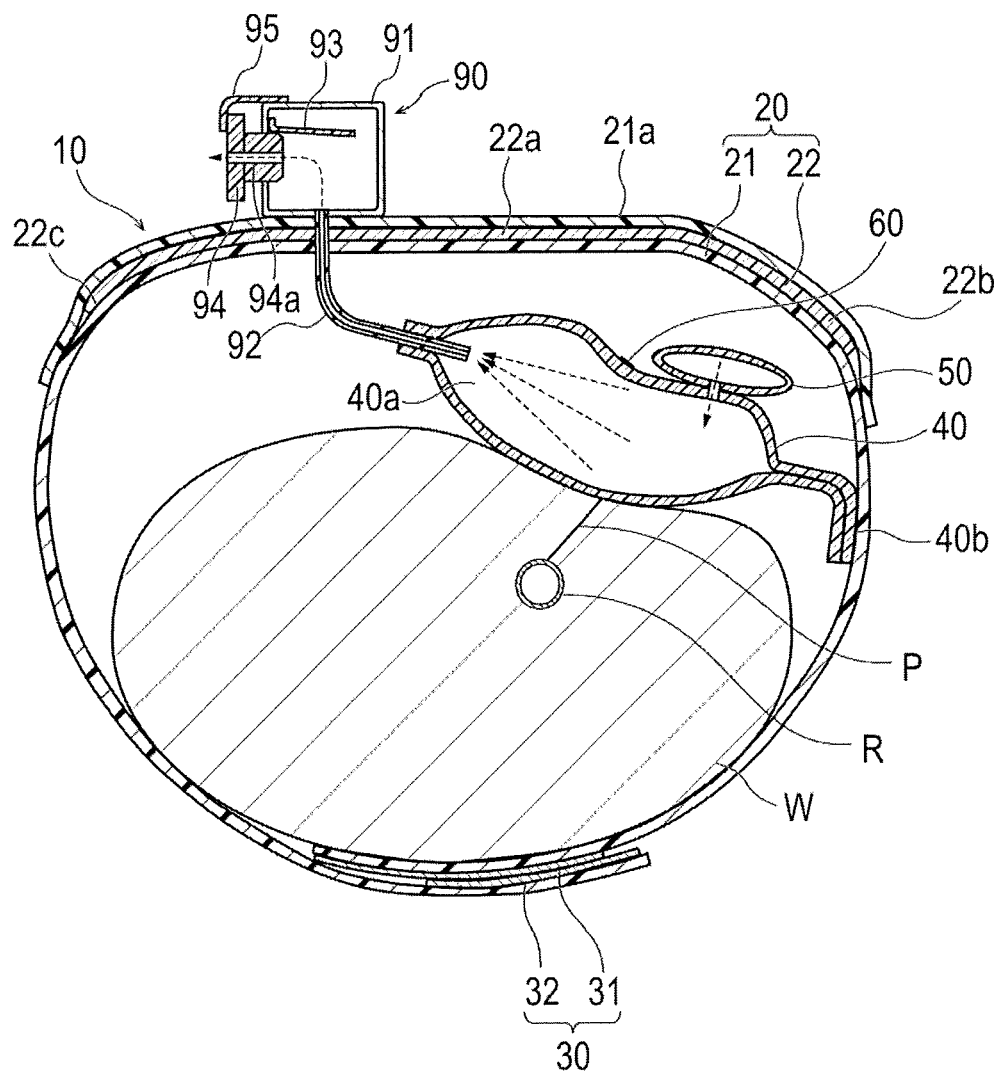
FIG. 12 is a sectional view taken along line 11-11 in FIG. 8, and is a view illustrating a state where the inflation portion is deflated.

A through-hole 91a penetrating the discharge port 91 in the thickness direction is disposed in the discharge port 91. As illustrated in FIG. 3, it is preferable to dispose the through-hole 91a on the side surface. In this manner, as illustrated in FIG. 12, a pushing force for pushing the switching member 94 into the through-hole 91a is applied in a direction orthogonal to the direction in which the puncture site P is pressed. Therefore, it is possible to prevent a disadvantage that the puncture site P is compressed more than necessary.

In order to prevent a disadvantage that the air contained in the discharge port 91 flows back to the inflation portion 40 after the discharge port 91 is pressed down and unintentionally contracted, it is preferable that the discharge port 91 is formed of a relatively rigid material which can maintain a constant shape. For example, as this material, it is possible to use a material the same as that of the support plate 22.

The valve 93 is disposed on the inner surface side of the discharge port 91 so as to close the through-hole 91a. In the valve 93, only a portion of the peripheral edge portion of the valve 93 is attached to the inner surface side of the discharge port 91. Therefore, as illustrated in FIG. 12, the switching member 94 can be inserted into the through-hole 91a.

It is preferable that the valve 93 is configured to include a flexible material. For example, it is possible to use a material the same as that of the band 20.

The switching member 94 is configured so that the switching member 94 can be inserted into and removed from the through-hole 91a. According to the exemplary embodiment, the switching member 94 is provided with a shape in which two columns having different diameters are connected to each other while being coaxially arrayed in parallel. In the switching member 94, a column portion having a small diameter is inserted into the through-hole 91a of the discharge port 91. In a state where the switching member 94 is inserted into the through-hole 91a, a column portion having a large diameter in the switching member 94 is in a state of protruding outward from the discharge port 91. The switching member 94 can be removed from the through-hole 91a by pulling the protruding portion. Note that, a shape of the switching member 94 is not particularly limited as long as the switching member 94 can be removed from the through-hole 91a.

In addition, a discharge lumen 94a penetrating the switching member 94 in the axial direction is formed in the switching member 94.

Figure 11:
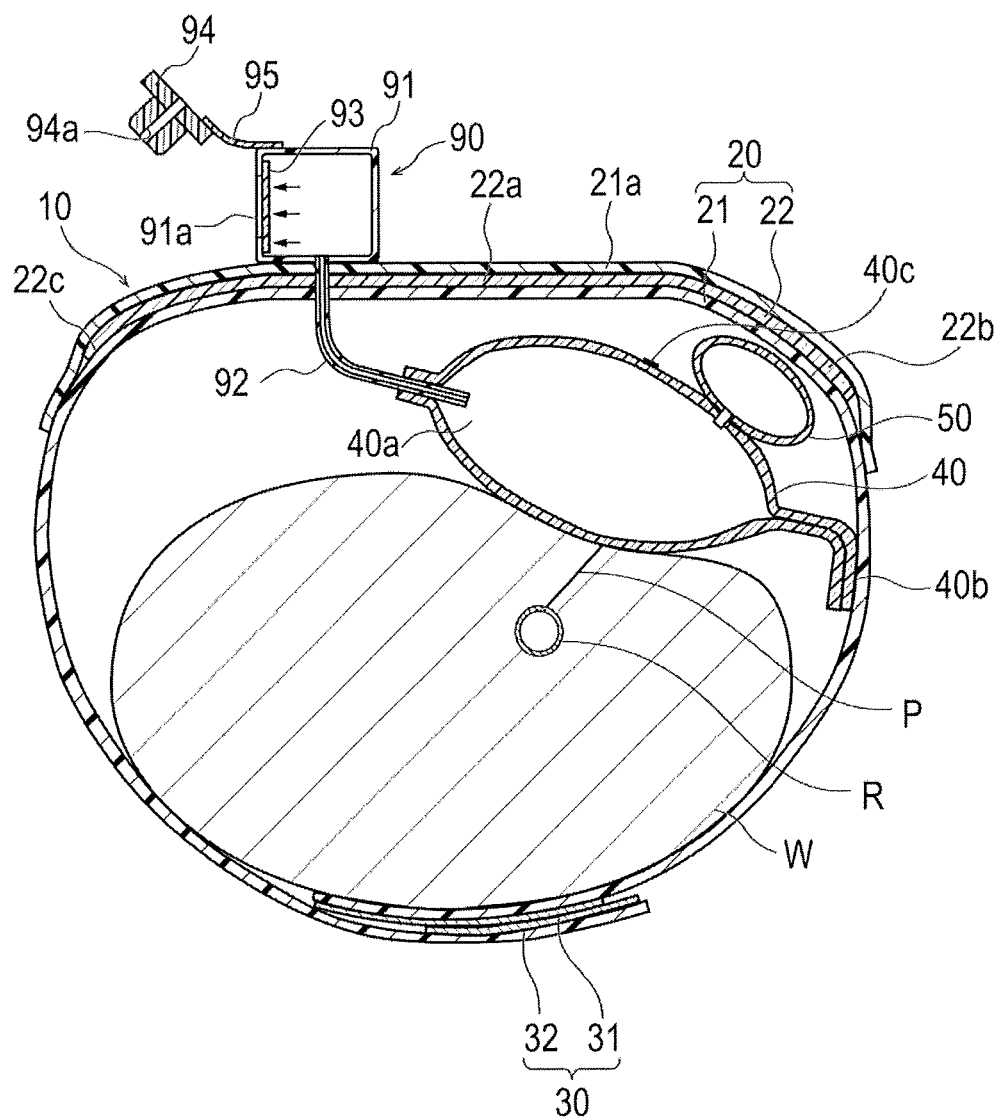
FIG. 11 is a sectional view taken along line 11-11 in FIG. 8, and is a view illustrating a state where the inflation portion is completely inflated.

As illustrated in FIG. 11, in a state where the switching member 94 is not inserted into the through-hole 91a of the discharge port 91, the through-hole 91a is closed by the valve 93. Therefore, the air contained in the inflation portion 40 is not discharged outward.

As illustrated in FIG. 12, in a state where the switching member 94 is inserted into the through-hole 91a of the discharge port 91, the internal space of the discharge port 91 and the outside communicate with each other by the discharge lumen 94a of the switching member 94, and thus, the air contained in the inflation portion 40 is discharged outward.

It is preferable that the interlock member 95 is configured to include a flexible material. For example, it is possible to use a material the same as that of the band 20.

Referring to FIGS. 7(A) and (B), an operation of the backflow prevention mechanism 82 will be described. In FIG. 7(A), a dotted line arrow indicates an air flow, and a solid line arrow indicates a direction of pressure applied to the covering member by the air.

As illustrated in FIG. 7(A), if the air is injected into the tube 81 from the injection portion 70 in a state where the inflation portion 40 is not sufficiently inflated, the air passes through the lumen 83a of the core member 83, and applies the pressure to the covering member 84 in a direction separated from the core member 83.

If the pressure received from the air sent from the injection portion 70 is equal to or greater than a predetermined magnitude, the covering member 84 is separated from the outer surface of the core member 83, thereby causing the distal opening portion 83c and the inflation space 40a to communicate with each other. For example, if the air amount sent from the injection portion 70 side is small since the operation for pressing down the injection portion 70 is not sufficiently performed, the pressure applied to the covering member 84 decreases. Accordingly, the distal opening portion 83c and the inflation space 40a cannot be caused to communicate with each other. In contrast, if the operation for pressing down the injection portion 70 is sufficiently performed by taking a relatively long time in slowly pressing the injection portion 70, the covering member 84 is separated from the outer surface of the core member 83. Note that, even in a case where the hole portion 74 of the injection portion 70 is erroneously closed by articles, if the operation for pressing down the injection portion 70 is not sufficiently performed, the air is not inadvertently sent into the inflation portion 40. Accordingly, it is possible to suitably prevent the puncture site P from being compressed more than necessary.

As illustrated in FIG. 7(B), in a state where the inflation portion 40 is sufficiently inflated, the air contained inside the inflation portion 40 applies the pressure to the covering member 84 in a direction in which the covering member 84 comes into contact with the core member 83. In this manner, the distal opening portion 83c is closed by the covering member 84. Accordingly, the air contained inside the inflation portion 40 does not flow back to not only the core member 83 side but also the injection portion 70 side. In addition, in a state where the inflation portion 40 is sufficiently inflated, the air contained inside the inflation portion 40 applies the pressure to the covering member 84 so as to close the distal opening portion 83c. The pressure becomes higher than air injection pressure. Therefore, if the internal pressure of the inflation portion 40 reaches a predetermined value after the inflation portion 40 is sufficiently inflated, the air cannot be injected into the inflation portion 40 from the injection portion 70. In this manner, in a state where the inflation portion 40 is sufficiently inflated, it is possible to suitably prevent the puncture site P from being compressed more than necessary by the inflation portion 40 being excessively inflated after the air is injected into the inflation portion 40 more than necessary.

Next, an example of using the hemostatic device 10 according to the exemplary embodiment will be described.

Before the hemostatic device 10 is worn on the wrist W, the inflation portion 40 is in a non-inflated state as illustrated in FIG. 2. As illustrated in FIGS. 8 and 9, in a case where the radial artery R of the wrist W of the right hand is punctured, the puncture site P is located close to the thumb side. Normally, the introducer sheath indwells the puncture site P. The band 20 is wrapped around the wrist W left in a state where the introducer sheath indwells the puncture site P. The marker 40c disposed in the inflation portion 40 aligns with the inflation portion 40 and the band 20 so as to overlap the puncture site P from above. The male side 31 and the female side 32 of the surface fastener 30 are brought into contact with and joined to each other. In this manner, the band 20 is worn on the wrist W.

After the hemostatic device 10 is worn on the wrist W, as illustrated in FIG. 9, the injection portion 70 is pressed down by pressing the vertical wall portion 71 while the hole portion 74 of the injection portion 70 is closed by the finger. According to this operation, the air contained inside the injection portion 70 is injected into the inflation portion 40, thereby dilating the inflation portion 40 and the auxiliary compression portion 50. The inflation portion 40 is inflated by the injection portion 70 integrated with the inflation portion 40. Accordingly, a physician or a nurse does not need to carry a separate dedicated instrument (syringe or the like) for dilating the inflation portion 40.

After the inflation portion 40 is inflated, the introducer sheath is removed from the puncture site P.

After the introducer sheath is removed, in accordance with a hemostatic progress condition or an elapsed time, the air amount to be sent to the inflation portion 40 and the auxiliary compression portion 50 may be adjusted by the injection portion 70 and the discharge portion 90. In this manner, the compressing force to be applied to the puncture site P by the inflation portion 40 may be adjusted. For example, if the inflated inflation portion 40 continues to compress the puncture site P and the blood vessel or the nerve around the puncture site P for a long time, there is a possibility that numbness or pain may be caused or the blood vessel may be occluded. In order to prevent the vascular occlusion, the discharge portion 90 discharges the air contained inside the inflation portion 40 with the lapse of time after the inflation portion 40 is inflated. A decompressing operation for gradually decreasing the internal pressure of the inflation portion 40 is performed. In this manner, the compressing force acting on the puncture site P may be decreased with the lapse of time. In this way, the decompressing operation can be performed by the discharge portion 90. Accordingly, a physician or a nurse can save time and effort as compared to carrying a separate dedicated instrument (syringe or the like) for performing the decompressing operation.

After the inflation portion 40 is inflated, the injection portion 70 is folded as illustrated in FIG. 10. Since the injection portion 70 is folded, it is possible to prevent the surrounding article or the finger from erroneously touching the injection portion 70.

If the hemostasis is completely performed on the puncture site P after a predetermined time elapses, the hemostatic device 10 is detached therefrom. The hemostatic device 10 is detached from the wrist W by separating the male side 31 and the female side 32 of the surface fastener 30 from each other. Note that, the hemostatic device 10 may be detached therefrom after the air contained inside the inflation portion 40 is discharged by the discharge portion 90.

As described above, the hemostatic device 10 according to the exemplary embodiment includes the band 20 for being wrapped around the wrist W, the securing means 30 for securing the band 20 in a state where the band 20 is wrapped around the wrist W, the inflation portion 40 that interlocks with the band 20, and that is inflated by injecting the air, and the injection portion 70 that can inject the air into the inflation portion 40. The injection portion 70 is disposed in the band 20, and is foldable so as to decrease the accommodation space 73 formed inside the injection portion 70.

According to the hemostatic device 10 configured as described above, the air is injected into the inflation portion 40 by the injection portion 70 which communicates with the inflation portion 40. Therefore, without using a separate dedicated instrument, a physician or a nurse can dilate the inflation portion 40. In addition, after dilating the inflation portion 40, the injection portion 70 is foldable so as to decrease the accommodation space 73 of the injection portion 70. Since the injection portion 70 is folded, there is a low possibility that the injection portion 70 may be further pressed down and the air may be further injected into the inflation portion 40. Accordingly, the hemostatic device 10 according to the exemplary embodiment can suitably prevent a disadvantage that the puncture site P is compressed more than necessary.

The injection portion 70 has the first side surface 71a, the second side surface 71b whose inner periphery and outer periphery are larger than those of the first side surface 71a, and the interlock portions 71d and 71e which interlock the first side surface 71a and the second side surface 71b with each other. In a state where the injection portion 70 is folded, the second side surface 71b covers the outer periphery of the first side surface 71a. Therefore, the injection portion 70 is more compactly foldable. In addition, the second side surface 71b has a larger inner periphery and outer periphery than the first side surface 71a. Accordingly, a volume of the injection portion 70 increases as the injection portion 70 is separated from the band 20. Since a portion (portion having the second side surface 71b formed therein) formed to have a larger volume in the injection portion 70 is pressed down, the air can be efficiently sent into the inflation portion 40 from the injection portion 70.

In addition, the injection portion 70 has the plurality of side surfaces 71a, 71b, and 71c, and the plurality of interlock portions 71d and 71e interlocking the adjacent side surfaces 71a, 71b, and 71c with each other. The side surface 71a disposed at the position close to the band 20 side has the smaller inner periphery and outer periphery relative to the side surfaces 71b and 71c disposed at the position separated from the band 20. According to the hemostatic device 10 configured in this way, as the injection portion 70 is closer to the band 20, the inner periphery and the outer periphery of the side surface decreases. Accordingly, the injection portion 70 is more easily foldable toward the band 20 side.

In addition, in a state where the injection portion 70 is unfolded, the interlock portions 71d and 71e between the adjacent side surfaces 71a, 71b, and 71c tilt or angle to a plane between the parallel side surfaces 71a, 71b, and 71c. Therefore, the injection portion 70 is easily foldable using a smaller force.

In addition, the injection portion 70 has the securing mechanism 72 which fixes the injection portion 70 in a state where the injection portion 70 is folded. Therefore, in the state where the injection portion 70 is folded, it is possible to prevent the injection portion 70 from being unintentionally brought into an unfolded state.

In addition, the injection portion 70 has the accommodation space 73 which can accommodate the air, and the hole portion 74 which communicates with the accommodation space 73. Therefore, the vertical wall portion 71 is folded while the hole portion 74 of the injection portion 70 is closed by the finger. In this manner, the inflation portion 40 can be inflated by injecting the air contained inside the injection portion 70 into the inflation portion 40.

In addition, the injection portion 70 has the rigid portion 75 which is much less likely to be deformed than other portions of the injection portion 70 when the injection portion 70 is folded. Therefore, when the injection portion 70 is folded, the pressing force is easily applied to the injection portion 70. Accordingly, the injection work can be easily carried out.

Figure 13:
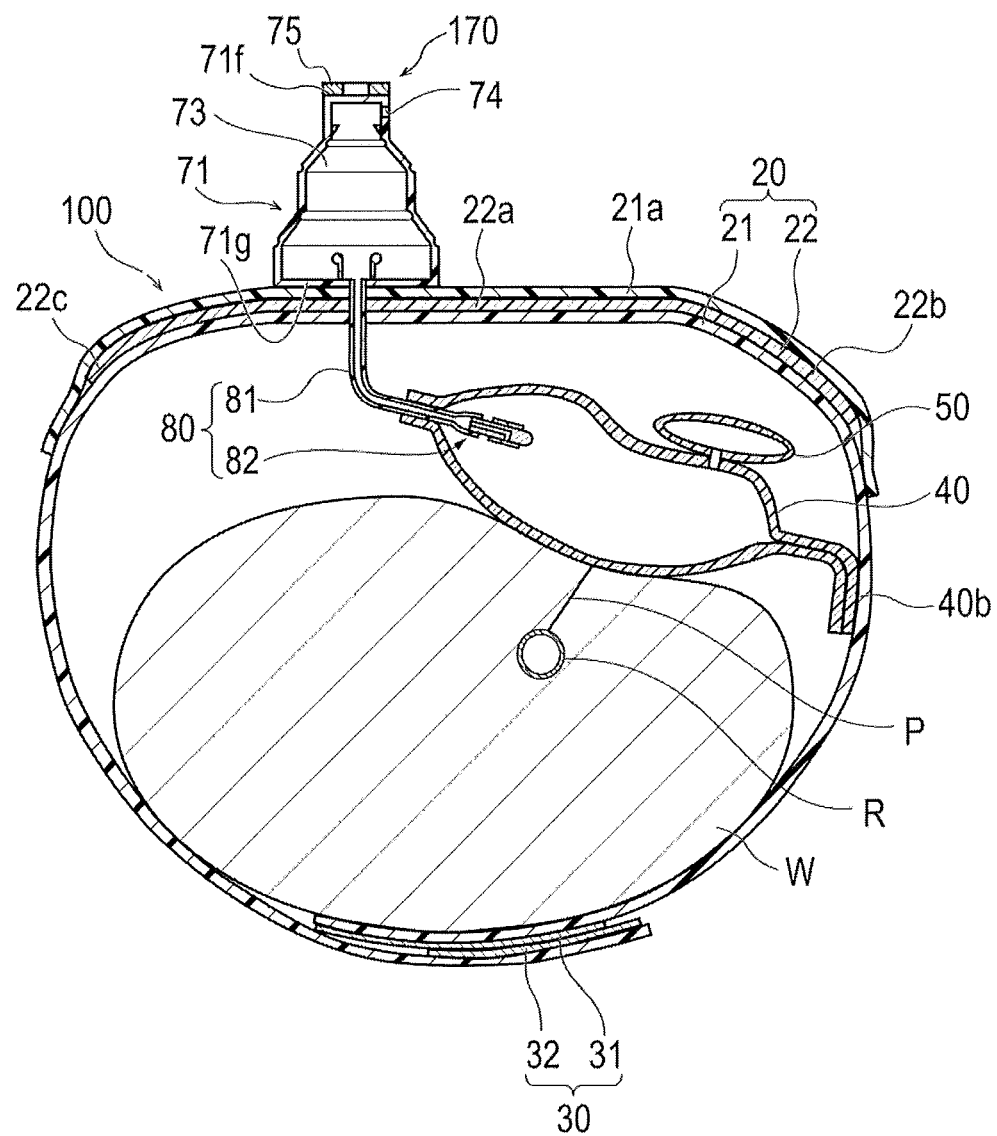
FIG. 13 is a sectional view of a hemostatic device according to a first modified embodiment of the disclosure.

FIG. 13 is a view for describing a hemostatic device 100 according to a first modified embodiment of the disclosure. Hereinafter, referring to FIG. 13, the hemostatic device 100 according to the first modified embodiment will be described. Note that, the same reference numerals will be given to configurations which are the same as those according to the above-described exemplary embodiment, and description thereof will be omitted.

In the hemostatic device 100 according to the first modified embodiment, a configuration of an injection portion 170 is different from that according to the above-described exemplary embodiment.

According to the above-described exemplary embodiment, the outer shape of the injection portion 70 is formed so that the outer periphery of the vertical wall portion 71 decreases as the injection portion 70 is closer to the band 20. On the other hand, according to the first modified embodiment, the injection portion 170 is formed so that the outer periphery of the vertical wall portion 71 increases as the injection portion 170 is closer to the band 20. Note that, the configuration itself of the injection portion 170 is the same as the configuration of the injection portion 70 according to the above-described exemplary embodiment. Disposing the band 20 by vertically inverting the injection portion 70 corresponds to the injection portion 170 according to the first modified embodiment of the disclosure.

As in the hemostatic device 100 according to the first modified embodiment, if the upper surface portion 71f in the injection portion 70 is formed to be smaller than the bottom surface portion 71g side, the upper surface portion 71f located at a position separated from the band 20 is formed to be relatively small. Accordingly, the surrounding articles are less likely to collide with the upper surface portion 71f side. In addition, when the injection portion 170 is folded, the respective side surfaces 71b and 71c can be disposed so as to be covered by the first side surface 71a located on the band 20 side. Accordingly, the injection portion 170 is compactly foldable.

Figure 14:
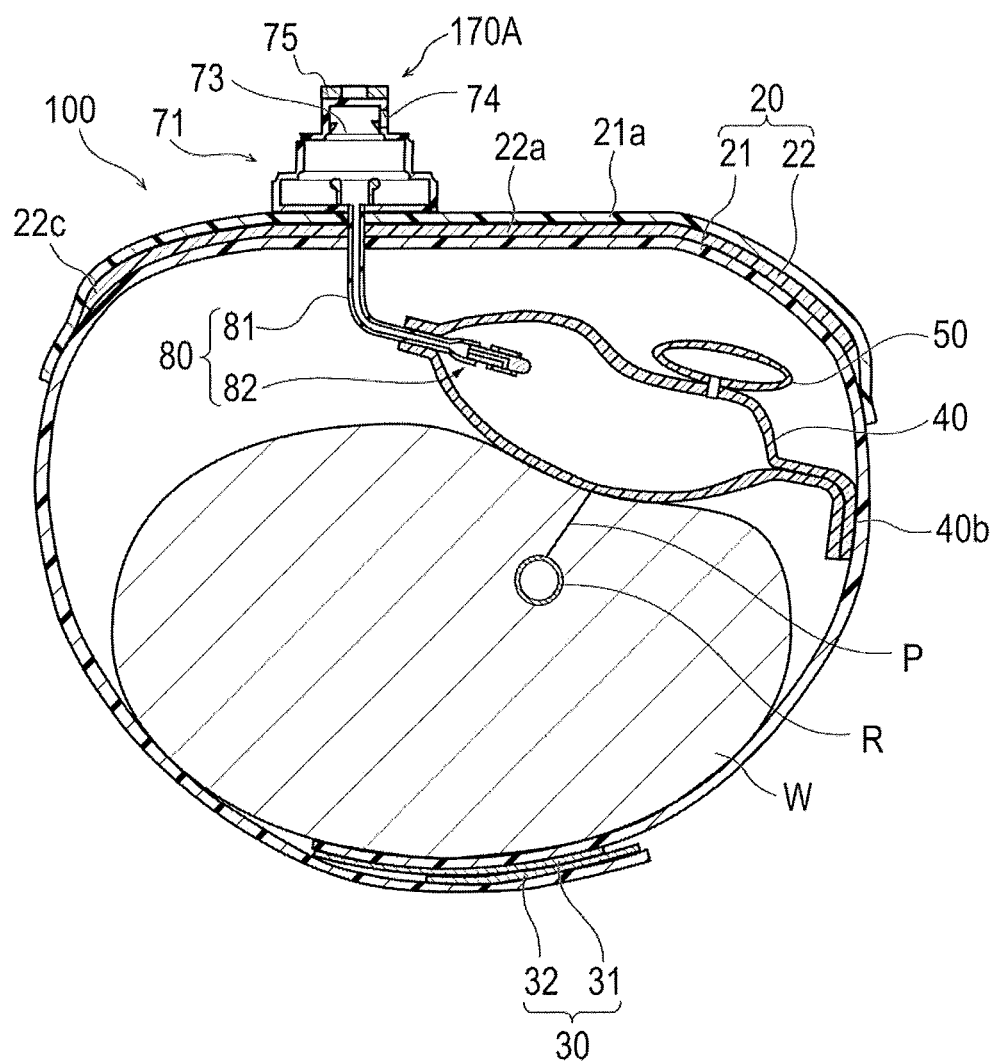
FIG. 14 is a sectional view illustrating an injection portion according to a modified example of the first modified embodiment.

Note that, as illustrated in FIG. 14, for example of a further modification of the hemostatic device 100, an injection portion 170A may be formed so that the interlock portions 71d and 71e are orthogonal to the vertical wall portion 71. Since the injection portion 170A is formed in this way, a shape of the injection portion 170A is simplified. Accordingly, it becomes easy to manufacture the hemostatic device 100. Note that, the injection portion 70 of the hemostatic device 10 according to the above-described exemplary embodiment may be similarly formed so that the interlock portions 71d and 71e are orthogonal to the vertical wall portion 71.

Figure 15:
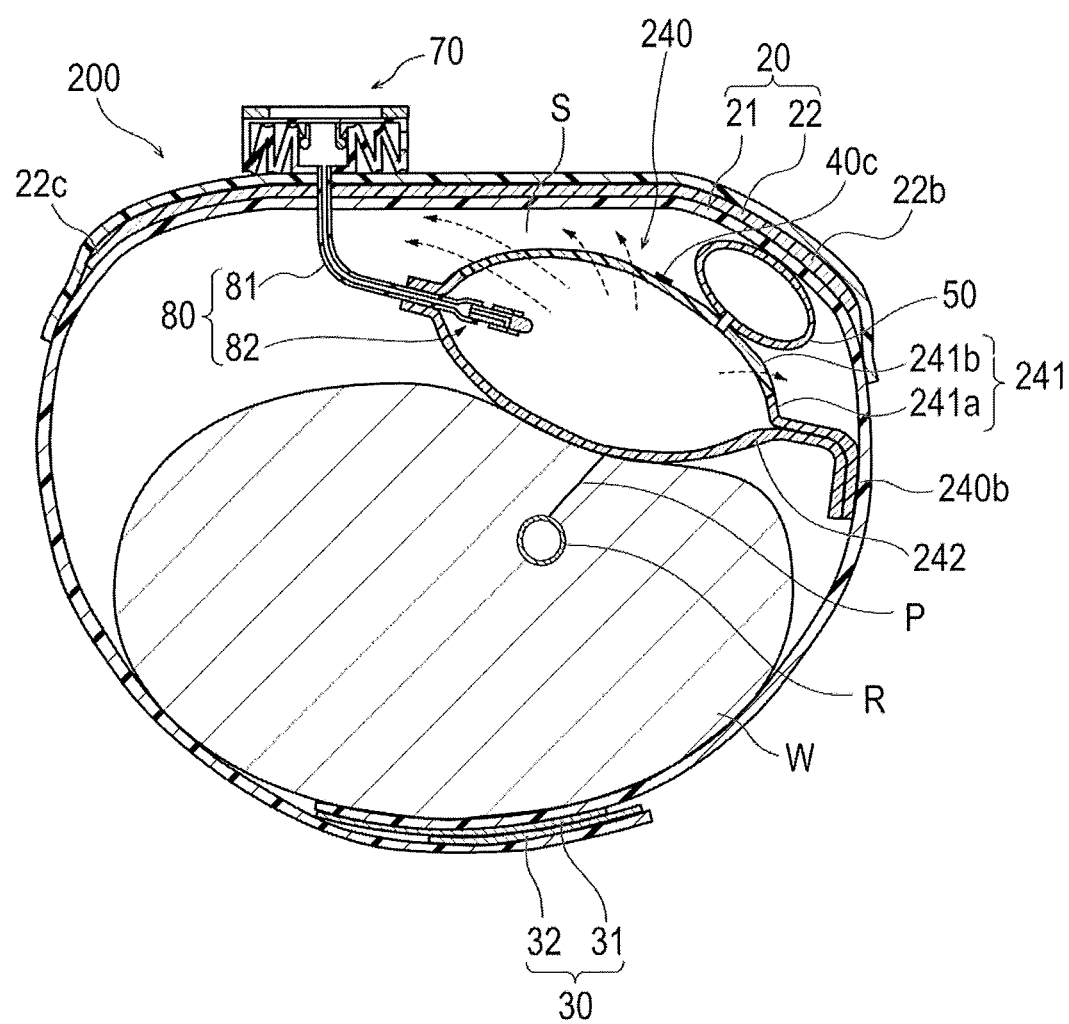
FIG. 15 is a sectional view of a hemostatic device according to a second modified embodiment of the disclosure.

FIG. 15 is a view for describing a hemostatic device 200 according to a second modified embodiment according to the disclosure. Hereinafter, referring to FIG. 15, the hemostatic device 200 according to the second modified embodiment will be described. Note that, the same reference numerals will be given to configurations which are the same as those according to the above-described embodiment, and description thereof will be omitted.

The hemostatic device 200 according to the second modified embodiment is different from that according to the above-described exemplary embodiment in that an inflation portion 240 is also provided with a function as a discharge portion which discharges the air contained in the inflation portion 240 outward.

As illustrated in FIG. 15, the inflation portion 240 is configured in a bag-like shape in which a first sheet 241 and a second sheet 242 which have a substantially rectangular shape overlap each other.

As illustrated in FIG. 15, the first sheet 241 includes a peripheral edge portion 241a configured to include a thermoplastic material, and a central portion 241b configured to include a thermosetting elastomer. Note that, according to the second modified embodiment, the thermosetting elastomer is disposed in the central portion of a surface on the band 20 side in the inflation portion 240. However, the thermosetting elastomer may be disposed in the central portion of a surface on the wrist W side in the inflation portion 240.

According to the second modified embodiment, the first sheet 241 is formed in such a way that the thermoplastic material and the thermosetting elastomer are respectively poured and integrally molded at a predetermined position in a mold having a predetermined shape. However, the first sheet 241 may be formed in such a way that a rectangular member (corresponding to the "central portion 241b") configured to include the thermosetting elastomer is disposed at the center of a frame-like member (corresponding to the "peripheral edge portion 241a") configured to include the thermoplastic material so as to bond both of these using an adhesive.

The second sheet 242 is configured to include the thermoplastic material.

As illustrated in FIG. 15, portions in which the peripheral edge portion 241a of the first sheet 241 and the peripheral edge portion of the second sheet 242 overlap each other are fused.

One side 240b inside the peripheral edge portion 241a of the first sheet 241 is fused to a side facing the wrist W of the belt 21 in the band 20.

The thermoplastic material used for the inflation portion 240 is not particularly limited. However, for example, it is possible to use the thermoplastic resin such as polyvinyl chloride, polyethylene, polypropylene, polyvinylidene chloride, or various thermoplastic elastomers such as olefinic thermoplastic elastomer, styrene thermoplastic elastomer, and polyethylene thermoplastic elastomer.

The thermosetting elastomer used for the inflation portion 240 employs those which have higher gas permeability than the thermoplastic material used for the inflation portion 240. For example, as the material, it is possible to use silicone or natural rubber. Therefore, in the inflation portion 240, after the inflation portion 240 is inflated, the air contained inside the inflation portion 240 is discharged outward from the inflation portion 240 with the lapse of time via a region formed of the thermosetting elastomer in the inflation portion 240 to such an extent that the vascular occlusion can be prevented (illustrated by a dotted line arrow in FIG. 15).

As described above, according to the hemostatic device 200 in the second modified embodiment, the gas contained inside the inflation portion 240 is discharged outward from the inflation portion 240 with the lapse of time via the region formed of the thermosetting elastomer in the inflation portion 240 to such an extent that the vascular occlusion can be prevented. Therefore, even if a physician or a nurse does not perform the decompressing operation, while the puncture site P is compressed, the compressing force acting on the puncture site P can be decreased with the lapse of time to such an extent that the vascular occlusion can be prevented. Therefore, it is possible to reduce the treatment burden or labor cost of the physician or the nurse.

In addition, in FIG. 15, the region formed of the thermosetting elastomer in the inflation portion 240 is disposed on a side facing the band 20. In addition, the auxiliary compression portion 50 is disposed between the region formed of the thermosetting elastomer in the inflation portion 240 and the band 20. Therefore, the auxiliary compression portion 50 forms a space S between the inflation portion 240 and the band 20. In this manner, in the region formed of the thermosetting elastomer in the inflation portion 240, the inflation portion 240 can increase an area of the exposed portion without coming into contact with the band 20. Therefore, the gas can be more satisfactorily discharged from the exposed portion.

Note that, the injection portion 70 (refer to FIG. 6(A)) according to the above-described exemplary embodiment is disposed in the hemostatic device 200 according to the second modified embodiment. However, it is also possible to dispose those which have the same structure as the respective injection portions 170 and 170A described in the first modified embodiment and the modified example thereof.

Hitherto, the hemostatic device according to the disclosure has been described with reference to the exemplary embodiment and the modified embodiments. However, without being limited to only the respectively described configurations, the disclosure herein can be appropriately modified based on the description in the appended claims.

For example, each portion configuring the hemostatic device can be substituted with any optional configuration which can fulfill the same function. In addition, any optional configuration element may be added thereto.

In addition, without being limited to the hemostatic device used by being worn on the wrist, the disclosure herein is also applicable to a hemostatic device used by being worn on a leg.

In addition, in the above-described exemplary embodiment, a case has been described where the hemostatic device includes the auxiliary compression portion. However, the auxiliary compression portion may not be provided.

In addition, in the above-described exemplary embodiment, the inflation portion interlocks with the band. However, the inflation portion may not directly interlock with the band. For example, a configuration may be adopted in which the circulation channel is disposed so as to penetrate the band, and the inflation portion is connected to an end portion on the inner surface side of the circulation channel. The band or the injection portion is connected to an end portion on the outer surface side of the circulation channel. In this manner, the inflation portion is prevented from being detached from the band. For example, in a case where the inflation portion of the hemostatic device in FIG. 2 sufficiently interlocks with the band by using the circulation channel, the inflation portion of each hemostatic device in FIGS. 2, 13, 14, and 15 may not interlock with the band via the holding portion.

In addition, in the above-described exemplary embodiment, a case has been described where the backflow prevention mechanism is disposed inside the inflation portion. However, a position of the backflow prevention mechanism is not particularly limited as long as the backflow prevention mechanism is disposed at any position between the inside of the inflation portion and the injection portion. In addition, depending on the disposed position, a configuration of the backflow prevention mechanism can be appropriately changed.

In addition, in the above-described exemplary embodiment, a case has been described where the hemostatic device includes the discharge portion. However, the discharge portion may not be provided. In addition, in the case where the hemostatic device includes the discharge portion, a configuration, a position, and a shape of the discharge portion are not particularly limited to the above-described exemplary embodiment as long as the gas contained inside the inflation portion can be discharged outward. For example, in the second modified embodiment, the region formed of the thermosetting elastomer is disposed in the central portion of the inflation portion. However, the region for disposing the thermosetting elastomer is not particularly limited. The whole inflation portion may be configured to include the thermosetting elastomer. In addition, for example, the hemostatic device may include both the discharge portion configured to include the discharge port according to the above-described exemplary embodiment and the inflation portion including the region formed of the thermosetting elastomer.

In addition, in the above-described exemplary embodiment, the vertical wall portion has the plurality of side surfaces and the plurality of interlock portions interlocking the adjacent side surfaces with each other. However, the injection portion is not limited to the above-described configuration as long as the injection portion is configured to be foldable.

In addition, in the above-described exemplary embodiment, the injection portion has three side surfaces and two interlock portions. However, the configuration is not particularly limited as long as the number of side surfaces is two or more. For example, the injection portion may be configured to have four or more side surfaces. In a case where the injection portion has four or more side surfaces, it is preferable that the inner periphery and the outer periphery of the side surface of the injection portion decrease as the inner periphery and the outer periphery are closer to the band.

In addition, in the above-described exemplary embodiment, the injection portion has the securing mechanism. However, the injection portion may not have the securing mechanism.

In addition, in the above-described exemplary embodiment, the injection portion has the rigid portion. However, the injection portion may not have the rigid portion.

In addition, in the above-described exemplary embodiment, the injection portion has the hole portion through which the air flows into the accommodation space. However, for example, instead of the hole portion, the injection portion may employ a structure having a check valve which can convey the air into the injection portion whereas the check valve prevents the air from flowing out from the injection portion.

The detailed description above describes features and aspects of embodiments of a hemostatic device. The disclosure is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A hemostatic device comprising:
a band for being wrapped around a hemostasis-requiring site of a limb;
securing means for securing the band in a state where the band is wrapped around the limb;
an inflation portion that interlocks with the band, and that is inflated by injecting gas; and
an injection portion that can inject gas into the inflation portion, the injection portion having an accommodation space which can accommodate the gas, an upper surface portion, and a hole portion that communicates with the accommodation space and is disposed below the upper surface portion,
wherein the injection portion is disposed on the band, and is configured to be foldable by moving the upper surface portion of the injection portion toward the inflation portion so as to decrease the accommodation space formed inside the injection portion, and to pressurize the gas and inject the pressurized gas into the inflation portion when the hole portion is closed and the injection portion is pressed and deformed to decrease the accommodation space,
wherein the injection portion has a securing mechanism for securing the injection portion in a state where the injection portion is folded,
wherein the injection portion has a plurality of side surfaces and the securing mechanism includes a first securing portion attached to an inner periphery of one of the plurality of side surfaces and a second securing portion configured to engage the first securing portion when the injection portion is folded, one of the first securing portion and the second securing portion being located below the hole portion in a state where the injection portion is not folded,
wherein the hole portion is disposed in one of said plurality of side surfaces.

2. The hemostatic device according to claim 1, wherein the injection portion has an interlock portion and the plurality of side surfaces include a first side surface and a second side surface, an inner periphery and an outer periphery of the second side surface being larger than an inner periphery and an outer periphery of the first side surface, and the interlock portion configured to interlock the first side surface and the second side surface with each other, and
wherein the second side surface covers at least a portion of the outer periphery of the first side surface, in a state where the injection portion is folded.

3. The hemostatic device according to claim 1, wherein the injection portion has a plurality of interlock portions interlocking adjacent side surfaces with each other, and wherein one of the plurality of side surfaces disposed at a position closer to the band side has an inner periphery and an outer periphery which are smaller than those of the plurality of side surfaces disposed at a position separated from the band.

4. The hemostatic device according to claim 3, wherein the plurality of interlock portions located between the adjacent side surfaces is angled relative to a plane parallel to the side surface, in a state where the injection portion is unfolded.

5. The hemostatic device according to claim 3, wherein the plurality of interlock portions located between the adjacent side surfaces are orthogonal relative to a plane parallel to the side surface, in a state where the injection portion is unfolded.

6. The hemostatic device according to claim 1, wherein the injection portion has a rigid portion which is less likely to be deformed than other portions of the injection portion when the injection portion is folded.

7. The hemostatic device according to claim 1, wherein the injection portion is integrated with the band.

8. A hemostatic device comprising:
a band adapted to be wrapped around a limb of a patient at a site on the limb where bleeding is to be stopped;
securing means for securing the band in a wrapped state around the limb;
an inflation portion disposed on an inner peripheral surface of the band, and adapted to be inflated by injecting gas; and
an injection portion adapted to inject gas into the inflation portion, the injection portion having an accommodation space which can accommodate the gas, an upper surface portion, a plurality of side surfaces, and a hole portion that is disposed in one of said plurality of side surfaces below the upper surface portion and is configured to provide communication between the accommodation space and an outside space,
wherein the injection portion is configured to be foldable by moving an upper surface portion of the injection portion toward the inflation portion so as to thereby decrease the accommodation space formed inside the injection portion, and to pressurize the gas and inject the pressurized gas into the inflation portion when the hole portion is closed and the injection portion is pressed and deformed to decrease the accommodation space, and the injection portion includes a securing mechanism adapted to maintain the injection portion in a folded state,
wherein the securing mechanism includes a first securing portion attached to a first portion of an interior surface of the injection portion, and a second securing portion attached to a second portion of the interior surface of the injection portion different from the first portion and configured to engage the first securing portion when the injection portion is folded, one of the first securing portion and the second securing portion being located below the hole portion in a state where the injection portion is not folded.

9. The hemostatic device according to claim 8, wherein the injection portion further includes a rigid portion, the rigid portion being less deformable than the plurality of side surfaces.

10. The hemostatic device according to claim 8, further comprising a circulation channel configured to provide communication between the accommodation space of the injection portion and the inflation portion.

11. The hemostatic device according to claim 10, wherein the circulation channel includes a backflow prevention mechanism.

12. The hemostatic device according to claim 8, further comprising a discharge portion configured to provide communication between the inflation portion and the outside space.

13. The hemostatic device according to claim 12, wherein the discharge portion includes a discharge port disposed on the band and a switching member configured to switch on and off communication between the discharge port and the outside space.

* * * * *